US00PP08477P

United States Patent [19]

Cripps

[11] Patent Number: Plant 8,477

[45] Date of Patent: Nov. 30, 1993

[54] APPLE TREE 'CRIPPS-TWO' CULTIVAR

[75] Inventor: John E. Cripps, Floreat Park, Australia

[73] Assignee: Chief Executive Officer of Dept. of Agriculture, South Perth, Australia

[21] Appl. No.: 862,782

[22] Filed: Apr. 3, 1992

[51] Int. Cl.[5] ..... A01H 5/00

[52] U.S. Cl. ..... Plt./34.1

[58] Field of Search ..... Plt./34.1, 35

[56] References Cited

U.S. PATENT DOCUMENTS

P.P. 7,880 6/1992 Cripps ..... Plt. 34.1

*Primary Examiner*—James R. Feyrer

*Assistant Examiner*—Erich E. Veitenheimer

*Attorney, Agent, or Firm*—Chernoff, Vilhauer, et al.

[57] ABSTRACT

A new variety of apple tree selected from a seedling population of a planned cross, characterized by the taste, low winter chilling requirements and its high dessert quality fruits which have good cold storage and retail shelf life.

5 Drawing Sheets

BACKGROUND AND SUMMARY OF THE INVENTION

This invention relates to a new and distinct variety of apple tree which was selected from a population of seedlings resulting from a planned cross between the varieties Lady Williams (unpatented chance seedling discovered in Western Australia) and Golden Delicious (unpatented chance seedling discovered in the State of West Virginia). The crosses were made in 1973 by John Cripps, Senior Research Officer, Western Australia Department of Agriculture at the Stoneville Horticultural Research Centre in Western Australia.

The new seedling variety first fruited in 1979 and was subsequently selected for propagation and further testing. Second, third and fourth generation trees have now borne fruit. It since has been recognized and selected as a new and improved apple variety which is distinctive from its parents as well as from all other apple varieties. The variety produces medium to large oblong-conical, uniquely flavored apples with a streaked red over-color on a yellow-green background which mature in late May to early June in Western Australia. It has not fruited in the United States. Its distinctive features include:

1. A spreading growth form and habit. Not as upright in growth habit as its sister seedling variety Cripps cultivar.
2. Low winter chilling requirements.
3. The ability to flower and fruit precociously and set fruit on one-year old upright growth. No tendency toward biennial bearing has been noted.
4. Fruit having high tolerance to sunburn and a medium thick skin which neither cracks nor is prone to russet, unlike its Golden Delicious parent.
5. Fruit having a medium flesh texture, and high acidity, which results in a crisp, fresh flavor with an appealing tang. In this respect, it differs from its parent Golden Delicious and from Fuji, both of which are sweeter to the taste.
6. Fruit having high soluble sugars of 12.5 to 15 percent Brix at optimum picking date.
7. Fruit having an ability to retain long retail shelf life, comparable to its sister variety, Pink Lady.

8. Fruit having a long cold storage life of up to six months allowing marketing flexibility.

Preliminary cold storage tests on apples harvested from three-year old trees grown at the Manjiump Research Centre indicate that this variety may not develop bitter pit and is highly tolerant to scald and as a consequence may not require DPA (Diphenylamine), as a preventive dip.

The variety has inherited the sunburn resistance, low chilling requirements exhibited by one of its parents (Lady Williams) and the excellent fruit quality (high sugar, crisp juicy flesh, and aromatic flavor) of both of its parent varieties.

The new seedling variety has been reproduced asexually by budding and grafting at the above named location. All subsequent asexually produced generations have been true to form in both their growth and fruiting characteristics and show that the foregoing characteristics come true and are established and transmitted through succeeding propagations and generations.

Figure 1:
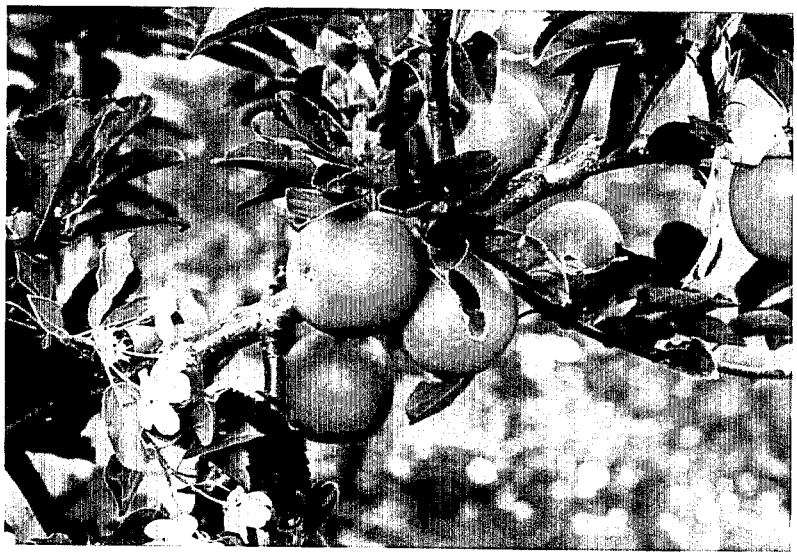
FIG. 1 shows a branch of the new variety apple tree bearing fruit.
Figure 2:
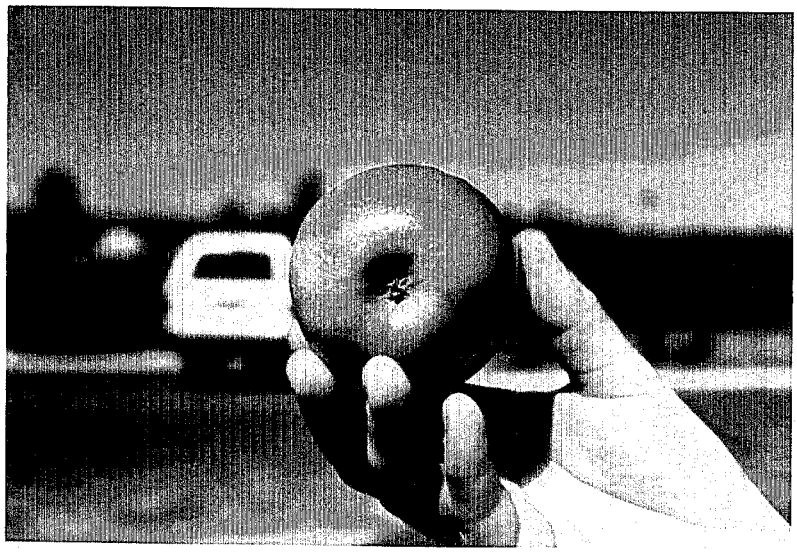
FIG. 2 is a close-up of the bottom of the new variety.
Figure 3:
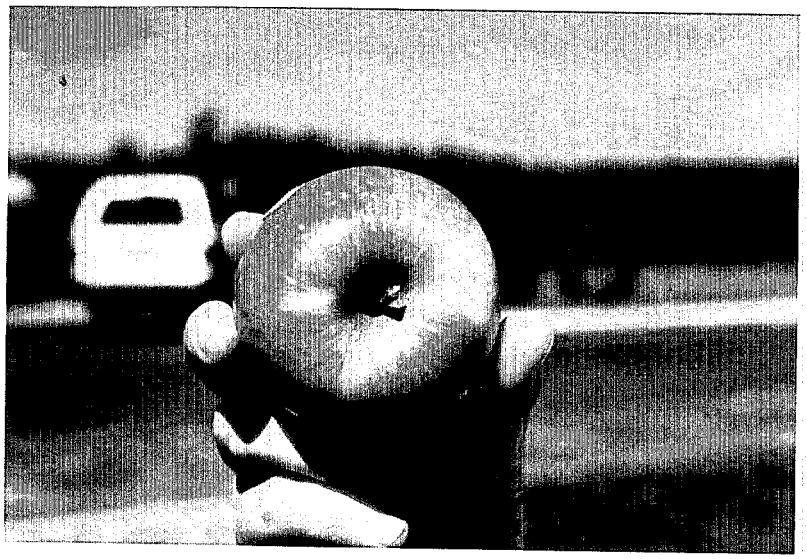
FIG. 3 is a close-up of the top of the new variety.
Figure 4:
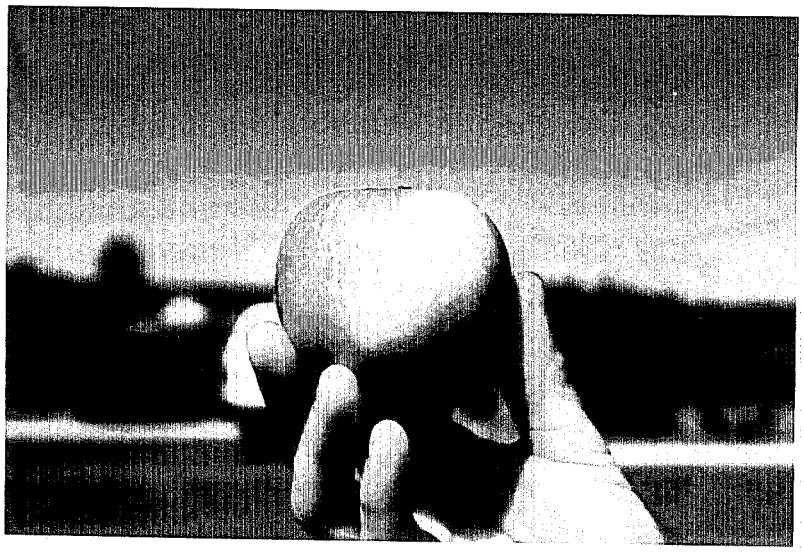
FIGS. 4 and 5 are close-ups of the side of fruit grown on the new variety.
Figure 5:
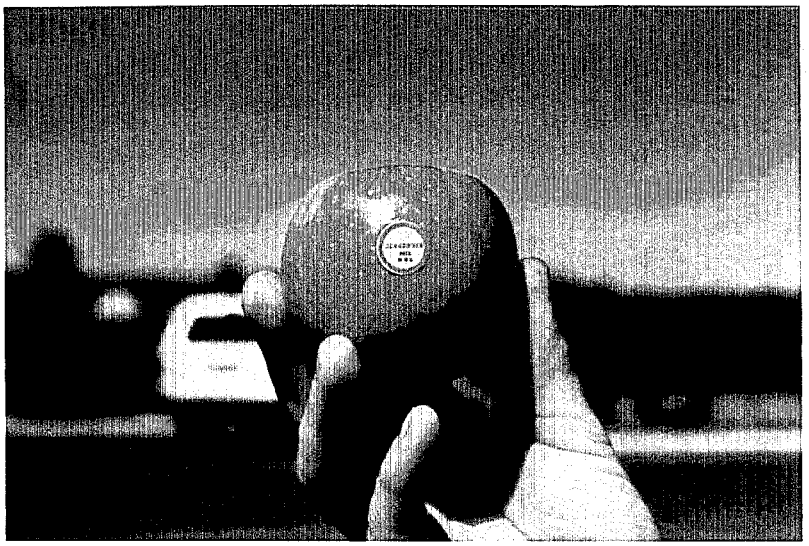
Figure 6:
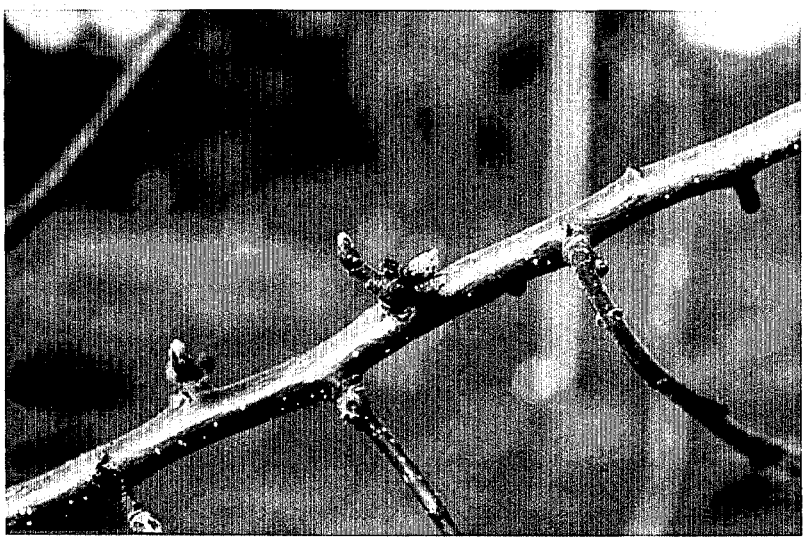
FIG. 6 shows a branch of the new variety.
Figure 7:
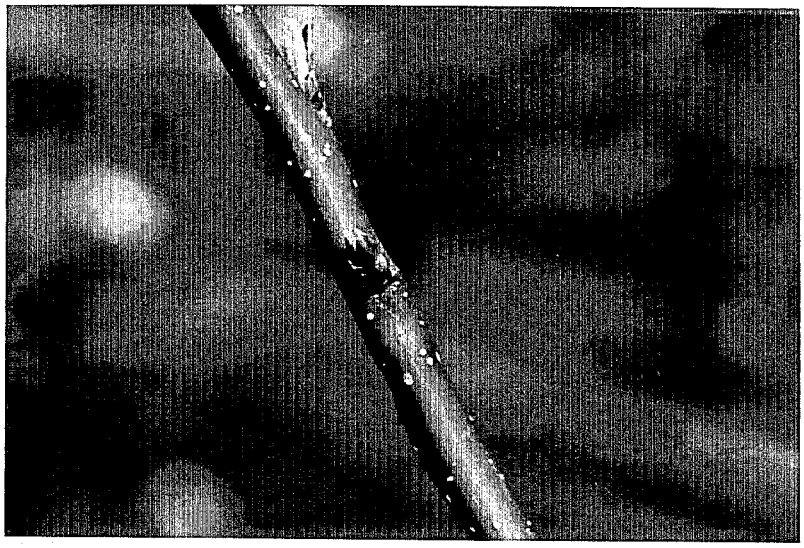
FIG. 7 shows the lenticels of the new variety.
Figure 8:
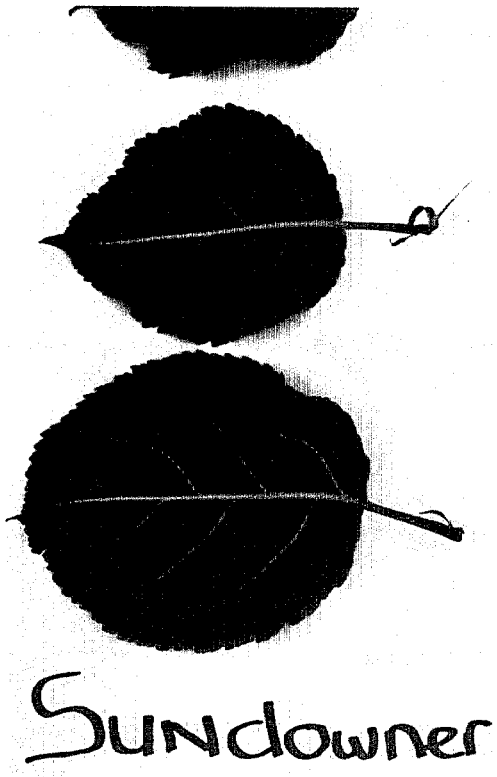
FIG. 8 shows the leaves of the new variety.
Figure 9:
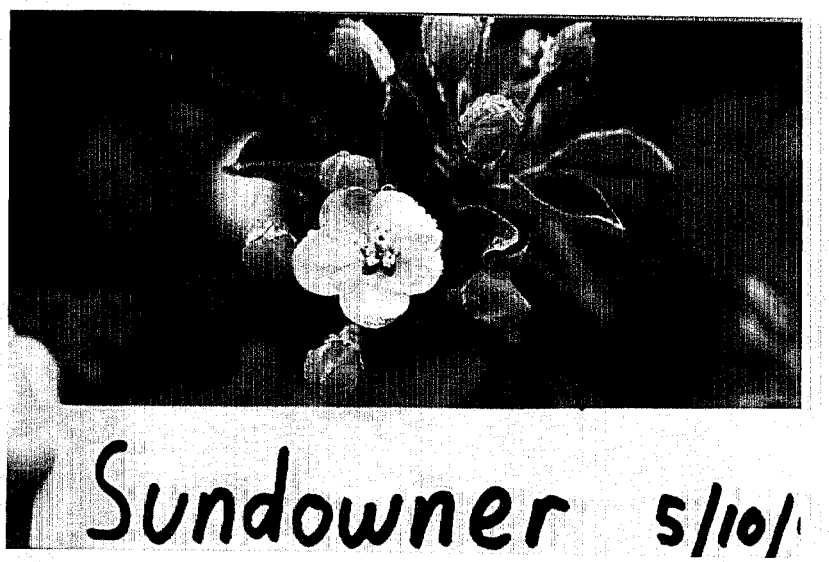
FIG. 9 shows the flowers of the new variety.
Figure 10:
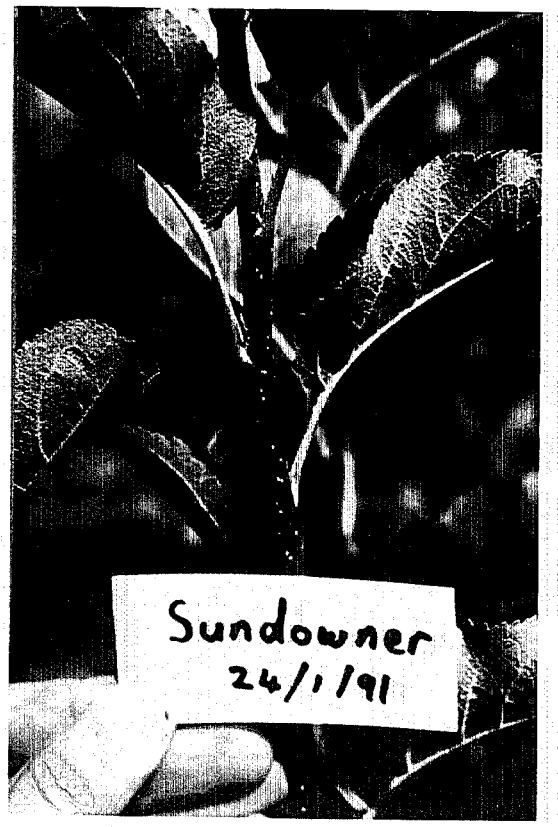
FIG. 10 shows the leaves of the new variety.

The following is a detailed description of the new apple variety with color terminology in accordance with the *Munsell Color Cascade Chart* except where general color terms of ordinary dictionary significance are used. Unless otherwise noted, all information is based on trees of the variety growing at the Manjiump Horticultural Research Centre, Western Australia. This variety is not in production in the U.S.

DETAILED DESCRIPTION OF THE INVENTION

Parentage: A cross of "Golden Delicious" and "Lady Williams" apple varieties.

Locality where grown and observed: Manjiump Horticultural Research Centre, Western Australia.

Dates of first and last pickings: About May 20 and June 4, respectively.

Tree: Medium to large with dense foliage. spreading habit, unpruned height to width ratio approximately 1.2 to 1.0 after 3 years.

*Predominance of bearing.*—Bears on both spurs and shoots.

*Vigor.*—Moderately vigorous, young trees average about 1.6 meters of new growth during the growing season in the nursery row following bud placement.

*Trunk.*—Medium stocky, smooth.

*Branches.*—Medium thick, smooth, wide angles to trunk.

*Branching habit.*—Much branched with average branching angles (inside measurement) of 60° if allowed to grow naturally.

*Pruning and training requirements.*—Dependent upon the dwarfing ability of the rootstock used. Adaptable to several styles, but best suited to "central leader" or "central axis" type training if trellising is employed.

*Pubescence.*—Medium (dormant one year old shoot).

*Thinning requirements.*—Not subject to the annual bearing habits of some apple cultivars. Use of common chemical thinning methods for non-annual bearing varieties should be employed.

*Color.*—Grey-brown (22-13) on side exposed to sun.

*Shape of tipbud.*—Rounded.

*Lenticels.*—Numerous, large, prominent.

*General pose.*—Outward.

*Size.*—Medium.

*Length.*—98 mm.

*Width.*—59 mm.

| Variety | Average Leaf Length (mm)* | Average Leaf Width (mm)* |
|---|---|---|
| Cripps-Two | 106.8 | 67.3 |
| Granny Smith | 98.0 | 51.7 |
| Gala | 98.7 | 60.8 |
| Hi-Early | 88.0 | 54.7 |
| Golden Delicious | 99.3 | 60.8 |

*Data from 1990–1991 season.

*Color.*—Green (20-12), glossy on upper surface, green (20-9) with slight pubescence on lower surface.

*Margin.*—Finely serrate, crenate.

*Petiole.*—Long, medium slender, pubescent. Color — Light green (21-10).

*Stipule.*—Small.

| Variety | Average Stipule Length (mm)* | Average Petiole Length (mm)* |
|---|---|---|
| Cripps-Two | 6.8 | 30.0 |

-continued

| Variety | Average Stipule Length (mm)* | Average Petiole Length (mm)* |
|---|---|---|
| Granny Smith | 4.6 | 30.6 |
| Gala | 13.0 | 27.6 |
| Hi-Early | 6.0 | 28.3 |
| Golden Delicious | 10.8 | 27.9 |

*Data from 1990–1991 season.

*Central leaf vein.*—Color — light green (19-5) with pink tinge toward basal end.

Flowers: Early (10% open flower), large.

*Dates of first and full bloom.*—About September 30 and November 25, respectively. In detailed flowering and pollination assessment, undertaken at the Manjiump Horticultural Research Centre during 1989 and 1990, Cripps-Two flowered earlier and for a longer period than Granny Smith, HiEarly, Gala, Golden Delicious, Lady Williams, and Fuji. Since this cultivar has not been grown in the USA, no blooming or harvest dates are available for local conditions.

*Size.*—Large.

*Color.*—Pinkish-red (closed) then white tinged with pink (open).

*Dormant fruit bud shape.*—Conical.

*Position of margin of petals.*—Free to touching.

Fruit:

*Maturity when described.*—Eating ripe.

*Size.*—Medium. Average diameter — 78.7 mm compared to 73.7 mm for Gala variety. Average weight — about 185 grams compared to 171 grams for Gala variety.

*Production.*—Fifth-year trees at Manjiump Horticultural Centre bore 4.3 bushels per tree per year with average crop size of 88 count.

*Coloration.*—Streaked red over-color on a yellow-green 23-10 background. Percentage of red over-color is up to 80% on fruit in full sun.

*Shape.*—Oblong conical distal crowns almost absent, rounded at base, sides equal, symmetric.

*Axis.*—Vertical.

*Ribbing.*—Absent.

*Cavity.*—Deep (18.4 mm), medium width (34.1 mm), average of 10 fruits.

*Basin.*—Open, medium width (30.6 mm), depth (11.4 mm), average of 10 fruits.

*Sepals.*—Medium, touching.

*Stem.*—Medium length (26.0 mm), medium thickness (2.2 mm), not lipped.

*Calyx.*—Closed, V-shaped, wide and medium depth. Calyx lobes — Reflexed and divergent. Pubescence — Slight.

*Skin.*—Smooth, some greasiness. Bloom — absent. Cracking tendency — absent. Thickness — medium. Ground color — yellow-green (23-10). Percentage of red overcolor — up to 80% on fruit in full sun. Overcolor of skin — red stripes, fills to solid red (39-14). Russet — Slight around stalk cavity. Lenticels — Large, prominent. Ripening — Very late (about May 20–June 4 in Western Australia). Firmness — Very firm. Pressure at harvest — 7.7 kg./cm3.* Percent of sugar at harvest — 13.2%.* Pressure 3-month cool storage — 6.6 kg./cm3.* Percent of sugar 3-month cool storage — 13.7%.*

* Data from apples harvested in 1990 season.

*Flesh.*—Color — Cream (26.2). Texture — Medium. Juiciness — Medium. Flavor — Acid tangy. Aroma — Non-distinct. Browning of flesh-weak.

*Core.*—Median. Bundle area — Small, symmetrical. Halves of area — Equal. Bundles — Inconspicuous. Core lines — Meeting, heart-shaped. Cross section — Indistinct. Calyx tube — Funnel-form. Pubescence — Slight. Stem or funnel — Short. Depth of tube to shoulder — About 4 mm. Entire depth — About 9 mm. Styles — United at base. Stamens — Median, in one whorl. Carpels — Nearly closed, axile, symmetrical, smooth, cordate form, emarginate at outer edge near tip.

Other characteristics:

*Seeds.*—One or two per cell, not tufted, acute at point, 7–8 mm long, 4 mm wide, obtuse, dark brown (31-15).

*Winter chill requirements.*—Estimated winter chilling requirements are less than 400 hours below 7° C. Potentially adaptable to temperature, mediterranean and partially subtropical climate zones.

Pollination: Not self-compatible, outside pollen sources help in setting a full crop in some seasons.

*Pollinator — Lady William % set.*—1988≈85%. 1989≈10%. 1990≈90%.

*Pollinator — Hi Early % set.*—1988≈75%. 1989≈85%. 1990≈90%.

*Pollinator — Granny Smith % set.*—1988≈90%. 1989≈5%. 1990≈N/A.

*Pollinator — Golden Delicious % set.*—1988≈65%. 1989≈0%. 1990≈90%.

*Pollinator — Gala % set.*—1988≈90%. 1989≈50%. 1990≈95%.

*Pollinator — Pink Lady % set.*—1988≈85%. 1989≈5%. 1990≈90%.

*Use.*—Dessert, market.

*Keeping quality.*—Good (up to six months in cold-room storage and 10–12 months in C.A. storage) Retail shelf life of approximately four weeks at temperatures of 15–18 degrees C.

What is claimed is:

1. A new variety of apple tree substantially as herein shown and described characterized by its ability to produce high quality dessert type late maturing fruits on spurs growing on upright limbs which possess firm, juicy, creamy-white flesh and excellent storage characteristics.

* * * * *